United States Patent
Marynka Kalmani et al.

(10) Patent No.: US 10,016,492 B2
(45) Date of Patent: Jul. 10, 2018

(54) METHODS FOR EXTRACTING A TOOTH

(71) Applicant: Proteolease Ltd., Ramat HaSharon (IL)

(72) Inventors: Keren Marynka Kalmani, Ramat Hasharon (IL); Evgeny Weinberg, Herzliya (IL); Yosef Gafni, Jerusalem (IL)

(73) Assignee: PROTEOLEASE LTD., Ramat Hasharon (IL)

(*) Notice: Subject to any disclaimer, the term of this patent is extended or adjusted under 35 U.S.C. 154(b) by 202 days.

(21) Appl. No.: 14/527,487

(22) Filed: Oct. 29, 2014

(65) Prior Publication Data

US 2015/0050617 A1 Feb. 19, 2015

Related U.S. Application Data

(63) Continuation of application No. PCT/IL2013/050367, filed on May 1, 2013.

(60) Provisional application No. 61/640,743, filed on May 1, 2012.

(51) Int. Cl.
*A61C 5/00* (2017.01)
*A61K 38/48* (2006.01)
*A61K 45/06* (2006.01)
*A61C 19/06* (2006.01)
*A61C 3/14* (2006.01)

(52) U.S. Cl.
CPC ........ *A61K 38/4886* (2013.01); *A61C 19/063* (2013.01); *A61K 38/48* (2013.01); *A61K 45/06* (2013.01); *C12Y 304/24003* (2013.01); *A61C 3/14* (2013.01); *C12Y 304/24007* (2013.01); *F04C 2270/041* (2013.01)

(58) Field of Classification Search
CPC .... A61K 38/4886; A61K 38/48; A61K 45/06; A61C 19/063
USPC ...................... 433/215, 217.1, 224
See application file for complete search history.

(56) References Cited

U.S. PATENT DOCUMENTS

| | | | |
|---|---|---|---|
| 5,139,944 A | 8/1992 | Sawyer et al. | |
| 5,709,873 A | 1/1998 | Bar-Shalom et al. | |
| 6,379,654 B1 | 4/2002 | Gebreselassie et al. | |
| 7,811,560 B2 | 10/2010 | Sabatino et al. | |
| 7,947,270 B2 | 5/2011 | Franklin | |
| 2005/0186526 A1 | 8/2005 | Stewart | |
| 2007/0224183 A1 | 9/2007 | Sabatino et al. | |
| 2008/0090208 A1* | 4/2008 | Rubbert ............ | A61C 13/0004 433/173 |

(Continued)

FOREIGN PATENT DOCUMENTS

DE 3719367 A1 12/1988
WO 2004041106 A1 5/2004

OTHER PUBLICATIONS

Kawada, Jiro, et al. "In Vitro Effects of Collagenase on Biomechanical Properties and Morphological Features of the Rat Molar Periodontal Ligament." Feb. 15, 2000. Japanese Journal of Oral Biology. vol. 43. pp. 193-205.*

(Continued)

*Primary Examiner* — Michael Carey
(74) *Attorney, Agent, or Firm* — The Roy Gross Law Firm, LLC; Roy Gross

(57) ABSTRACT

Methods of extracting teeth involving contacting, prior to extraction, the tissue surrounding a tooth to be extracted with a composition providing an agent capable of destroying the periodontal ligament surrounding the tooth, such as, collagenase.

17 Claims, 4 Drawing Sheets

(56) References Cited

U.S. PATENT DOCUMENTS

| | | | | |
|---|---|---|---|---|
| 2008/0233614 | A1* | 9/2008 | Cranenburgh | C12N 9/52 435/69.1 |
| 2009/0098509 | A1* | 4/2009 | Weathers | A61C 3/14 433/152 |
| 2009/0117092 | A1* | 5/2009 | Kappler | C12N 9/52 424/94.63 |
| 2009/0136897 | A1* | 5/2009 | Kappler | A61C 3/00 433/143 |
| 2009/0181342 | A1* | 7/2009 | Chien | A61C 1/07 433/119 |
| 2010/0061972 | A1 | 3/2010 | Smith | |
| 2010/0233151 | A1 | 9/2010 | Sabatino et al. | |
| 2010/0330065 | A1 | 12/2010 | Sabatino et al. | |
| 2011/0158972 | A1 | 6/2011 | Sabatino et al. | |
| 2011/0189153 | A1 | 8/2011 | Sabatino et al. | |
| 2011/0189163 | A1 | 8/2011 | Sabatino et al. | |
| 2011/0243908 | A1 | 10/2011 | Sabatino et al. | |
| 2011/0243909 | A1 | 10/2011 | Sabatino et al. | |
| 2011/0243919 | A1 | 10/2011 | Sabatino et al. | |
| 2011/0243920 | A1 | 10/2011 | Sabatino et al. | |
| 2012/0045816 | A1 | 2/2012 | Ghaderi et al. | |
| 2012/0237497 | A1 | 9/2012 | Wegman et al. | |
| 2013/0166040 | A1* | 6/2013 | Diekwisch | A61C 8/0012 623/23.57 |
| 2013/0287760 | A1 | 10/2013 | Nanchahal et al. | |
| 2014/0004094 | A1 | 1/2014 | Sabatino et al. | |
| 2014/0335072 | A1 | 11/2014 | Hart | |

OTHER PUBLICATIONS

Hiller et al., (2000) Matrix metalloproteinases collagenase-2, macrophage elastase, collagenase-3, and membrane type 1-matrix metalloproteinase impair clotting by degradation of fibrinogen and factor XII. J Biol Chem 275(42): 33008-13.

Stewart et al., (2005) Use of relaxin in orthodontics. Ann N Y Acad Sci 1041: 379-87.

Angleton and Van Wart (1988) Preparation and reconstitution with divalent metal ions of class I and class II Clostridium histolyticum apocollagenases. Biochemistry 27(19): 7406-12.

Komatsu et al., (2007) Analysis of contribution of collagen fibre component in viscoelastic behaviour of periodontal ligament using enzyme probe. J Biomech 40(12): 2700-6.

Komatsu et al., (2007) Stress-relaxation and microscopic dynamics of rabbit periodontal ligament. J Biomech 40(3): 634-44.

Komatsu et al., (2010) Mechanical Strength and Viscoelastic Response of the Periodontal Ligament in Relation to Structure. J Dent Biomech 2010: 502318.

Naveh et al., (2012) Tooth periodontal ligament: Direct 3D microCT visualization of the collagen network and how the network changes when the tooth is loaded. J Struct Biol 181(2): 108-15.

Naveh et al., (2012) Tooth-PDL-bone complex: response to compressive loads encountered during mastication—a review. Arch Oral Biol 57(12): 1575-84.

On Extraction of teeth, [online], Smile Dental Clinic, Feb. 23, 2010, obtain the file registered on Feb. 23, 2010 at http://web.archive.org/ (uploaded Jan. 27, 2017), Internet, URL, http://web.archive.org/web/20100223224854/http://www.smile-dc.net/backnumber/20100201.html ; 3 pages—English translation.

Toksvig-Larsen et al., (1991) On the problem of heat generation in bone cutting. Studies on the effects on liquid cooling. Bone & Joint Journal, 73(1), 13-15.

Wynn & Barron, (Aug. 2010) Macrophages: master regulators of inflammation and fibrosis. In Seminars in liver disease (vol. 30, No. 03, pp. 245-257). © Thieme Medical Publishers.

Yamane et al., (1991) The Influence of Collagenase Treating on the Mechanical Properties of Rat Lower Jaw Incisor Periodontal Ligament, Journal of Basic Dental Medicine, vol. 33 (Supplementary volume), p. 245—Translated abstract.

* cited by examiner

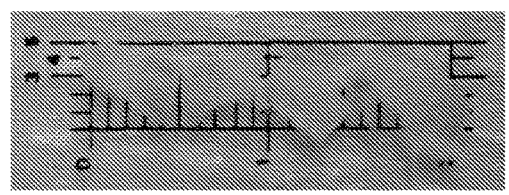
Figure 1
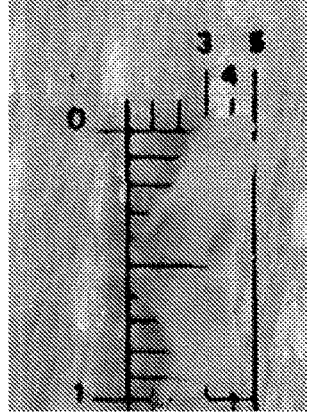
Figure 2A
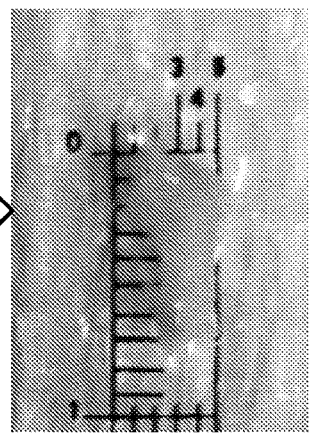
Figure 2B
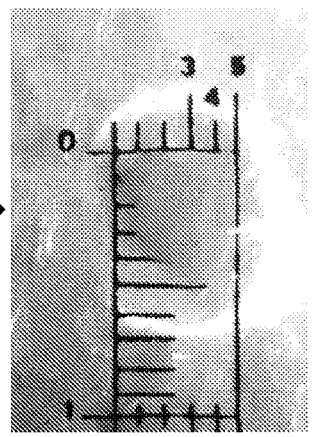
Figure 2C
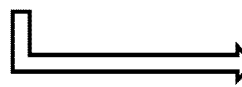
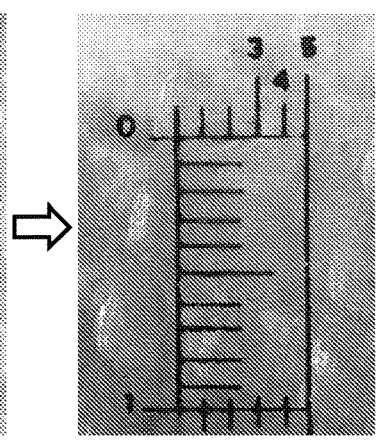
Figure 2D
Figure 2E

METHODS FOR EXTRACTING A TOOTH

FIELD OF THE INVENTION

The present invention is directed to methods of extracting teeth comprising contacting, prior to extraction, the tissue surrounding a tooth to be extracted with a composition comprising an agent capable of destroying the periodontal ligament surrounding the tooth, such as, collagenase. The present invention is further directed to method of replacing a tooth with dental implants following enzymatic extractions.

BACKGROUND OF THE INVENTION

Various dental procedures for extraction of a tooth are known in the art. Commonly, these methods involve luxating the tooth with dental elevator until the periodontal ligament is sufficiently broken and the supporting alveolar bone is adequately widened to make the tooth loose enough thereby ready to be removed. Removal of the tooth is usually accomplished with dental forceps through the application of intermittent apical and lateral forces. When a tooth cannot be easily accessed (e.g. because it is broken under the gum line), the surgical procedure may be involved, requiring elevation of the soft tissues covering the tooth and removal of some of the surrounding jawbone tissue with a drill, in order to access the tooth for extraction.

During and after such conventional dental procedures bleeding, fluid seepage or weeping, or other forms of fluid loss typically occur. In addition, bone tissue is being removed or damaged during the procedure. As a result, swelling and residual bleeding persist during the healing period. Generally, whether the injury to the surrounding tissues during extraction procedure is greater, these side effects are more pronounced.

Komatsu (J. Biomech., 40:634-644, 2007) discloses the alignment of collagen molecules and fibrils, during stress-relaxation of the PDL in a tooth-PDL bone segment.

Komatsu et al. (J. Biomech., 40: 2700-2706, 2007; and J. Dental Biomech., doi:10.406/2010/502318) disclose that collagenase reduced greater area occupied by the PDL collagen fibers, reduced birefringent retardation of the fibers and reduced the PDL fiber area in PDL specimen, in vitro.

There is an unmet need to minimize the adverse outcomes of tooth extraction, including pain, tissue injury and/or trauma, and to enable convenient reconstruction of edentulous area together with reduced treatment time and shorter healing period.

SUMMARY OF THE INVENTION

The present invention is directed to a method for reducing a risk associated with tooth extraction in a subject in need thereof, comprising applying an effective volume of a composition comprising an effective amount of an agent capable of destroying the periodontal ligament surrounding the tooth, such as, collagenase, into the periodontal ligament space of said tooth, thereby reducing the risks and excessive pain associated with tooth extraction in a subject in need thereof.

The present invention is based, in part, on the unexpected discovery that extracting a tooth by topical application, into the tissue surrounding a tooth, of an agent capable of severing the periodontal ligament surrounding the tooth, requires investing significantly less force compared to the force required for extracting a tooth using common methods. Moreover, the method of the invention ensures superior patient comfort and therefore patient compliance due to its advantageous features, such as, reduction in bleeding, reduction in tooth socket deformation, and minimal damage to the alveolar bone.

In one embodiment, the present invention provides a method for extracting a tooth in a subject in need thereof, comprising: (a) applying a composition comprising an effective amount of an agent into the tissue surrounding said tooth, the agent is capable of destroying the periodontal ligament surrounding the tooth; and (b) extracting said tooth.

In another embodiment, the agent is an enzyme, said enzyme is capable of cleaving or hydrolyzing collagen peptide bonds. In yet another embodiment, the enzyme is a proteolytic enzyme. In yet another embodiment, the enzyme is a protease. In yet another embodiment, the enzyme is a proteolytic enzyme capable of hydrolyzing or otherwise cleaving the peptide bonds in collagen. In yet another embodiment, the enzyme is selected from the group consisting of: dispase, collagenase, proteinase K, hyaluronidase and combinations thereof. Each possibility represents a separate embodiment of the invention.

In yet another embodiment, the composition further comprises an agent selected from the group consisting of: a pain killer, an anesthetic, an antibiotic, a narcotic, a vitamin, a growth factor and a flavoring agent. Each possibility represents a separate embodiment of the invention.

In yet another embodiment, extracting comprises applying an extraction force parallel to the long axis of said tooth, thereby minimizing damage of the tissue surrounding the tooth, bleeding and bone loss. In yet another embodiment, extracting is devoid of applying a rotational force.

In another embodiment, applying comprises contacting at least one locus at the periodontal ligament space surrounding the tooth. In another embodiment, contacting comprises injecting said composition into the intra periodontal ligament.

In another embodiment, the step of extracting said tooth is performed within 15 minutes to 3 hours after applying said composition.

In yet another embodiment, the agent capable of destroying the periodontal ligament surrounding the tooth is collagenase.

In yet another embodiment, the agent capable of destroying the periodontal ligament surrounding the tooth is an antibody against a collagen.

In yet another embodiment, said collagenase is selected from the group consisting of collagenase I, collagenase II, collagenase III and a combination thereof. Each possibility represents a separate embodiment of the invention. In yet another embodiment, said composition comprises 1 to 1 mass ratio of collagenase I to collagenase II. In yet another embodiment, said composition has an effective volume of 0.01 to 3 ml. In yet another embodiment, said composition has an effective volume of 0.1 to 2 ml.

In yet another embodiment, said subject in need thereof is a subject afflicted with a bleeding disorder.

In yet another embodiment, the method further comprises replacing said tooth by placing a dental implant at a cavity obtained following extracting said tooth.

In yet another embodiment, the present invention provides a method for extracting a tooth in a subject in need thereof, comprising: (a) injecting a composition comprising an effective amount of collagenase into a plurality of loci at the periodontal ligament surrounding the tooth; and (b) extracting said tooth at least 15 minutes after the injection of said composition.

In yet another embodiment, the method further comprises placing a dental implant at a cavity obtained following extracting said tooth.

In yet another embodiment, the present invention provides a method of replacing a tooth with a dental implant comprising: (a) applying a composition comprising an effective amount of collagenase to the periodontal ligament surrounding a tooth; (b) extracting said tooth at least 15 minutes after the applying said composition; and (c) placing a dental implant at a cavity obtained following extracting said tooth.

In yet another embodiment, applying comprises injection said composition into at least one locus at the periodontal ligament surrounding said tooth. In yet another embodiment, applying comprises injecting said composition into a plurality of loci at the periodontal ligament surrounding said tooth. In yet another embodiment, applying comprises injecting said composition into 2 to 8 loci at the periodontal ligament surrounding said tooth.

In yet another embodiment, the method further comprises applying an effective amount of a deactivation agent into the tissue surrounding said tooth, prior to extracting said tooth. In yet another embodiment, said deactivation agent is a chelating agent.

In yet another embodiment, said deactivation agent is ethylenediaminetetraacetic acid (EDTA) and derivatives thereof. In yet another embodiment, said deactivation agent is EDTA.

In yet another embodiment, the present invention provides kit for extracting a tooth, comprising a first container comprising a composition comprising an effective amount of an agent into the tissue surrounding said tooth; a second container comprising a composition comprising an effective amount of a deactivation agent; and instructions manual, listing the use of each component of the kit and the sequence of use.

In yet another embodiment, the kit further comprises a container comprising an agent selected from the group consisting of: a pain killer, an anesthetic, an antibiotic, a narcotic, a vitamin, a growth factor, a flavoring agent and combination thereof.

In yet another embodiment, the kit further comprises dental means for extracting said tooth.

In yet another embodiment, the present invention provides the use of an agent for loosening the periodontal ligaments of a tooth of a subject in need thereof, comprising applying to the periodontal ligaments surrounding a tooth an agent capable of destroying said periodontal ligaments of said tooth, thereby loosening the periodontal ligaments which anchor said tooth to its socket.

In yet another embodiment, the agent is an enzyme capable of cleaving or hydrolyzing peptide bonds at the periodontal ligament surrounding the tooth. In yet another embodiment, said agent is a proteolytic enzyme. In yet another embodiment, the enzyme is selected from the group consisting of: dispase, collagenase, proteinase K, hyaluronidase and combinations thereof. In yet another embodiment, the enzyme is collagenase. In yet another embodiment, said collagenase is selected from the group consisting of collagenase I, collagenase II, collagenase III and a combination thereof. In yet another embodiments, said composition comprises 1 to 1 mass ratio of collagenase I to collagenase II. In yet another embodiment, said composition has an effective volume of 0.01 to 3 ml.

In yet another embodiment, said composition further comprises an agent, selected from the group consisting of: a pain killer, an anesthetic, an antibiotic, a narcotic, a vitamin, a growth factor, a flavoring agent and combination thereof.

In yet another embodiment, the agent capable of destroying the periodontal ligament surrounding a tooth is an antibody against a collagen.

In yet another embodiment, applying comprises contacting at least one locus at the periodontal ligament space surrounding the tooth.

In yet another embodiment, said subject is afflicted with a bleeding disorder.

In yet another embodiment, the use further comprises applying an effective amount of a deactivation agent into the tissue surrounding said tooth, prior to extracting said tooth. In yet another embodiment, said deactivation agent is ethylenediaminetetraacetic acid. In yet another embodiment, the use comprises applying the effective amount of a deactivation agent 10 minutes to 3 hours after applying said composition.

In yet another embodiment, the use and method of the invention reduce a risk associated with tooth extraction in a subject in need thereof.

In yet another embodiment, the use and method of the invention accelerate restoration of the extracted tooth by permitting immediate placement of a dental implant in a subject in need thereof.

BRIEF DESCRIPTION OF THE DRAWINGS

FIG. 1 presents a slice of gingival tissue obtained from the diastema region of pig mandible.

FIGS. 2A-2E exhibit various slices of gingival tissue from the diastema region of pig mandible (panel 2A) following incubation for 3 hrs with PBS (panel 2B) and for 24 hrs with PBS (panel 2C) or following incubation for 3 hrs with collagenase (panel 2D) and for 24 hrs with collagenase (panel 2E).

DETAILED DESCRIPTION OF THE INVENTION

Figure 3A:
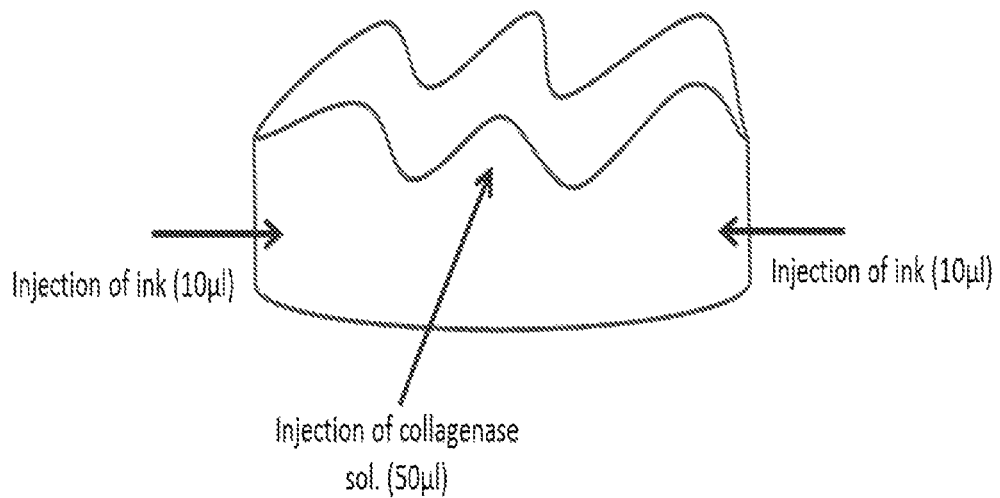
FIGS. 3A-3B are an illustration (FIG. 3A) and a representative slice (FIG. 3B) of the experimental set up used for visualizing collagen degeneration.

Other objects, features and advantages of the present invention will become clear from the following description.

The present invention provides a method for extracting a tooth or a fragment of the broken root of the tooth by enzymatically or biochemically severing the periodontal ligament fibers anchoring the tooth to its socket. In another embodiment, the present method includes contacting the periodontal ligament space with a composition comprising an agent capable of destroying the periodontal ligament surrounding the tooth. In one embodiment, the agent is collagenase and the PDL is made of collagen, such that, the collagenase breaks the peptide bonds in collagen. Accordingly, tooth extraction according to the method of the invention results with minimizing and even avoiding the need for applying rotational pressure and luxation forces in bucco-lingual and mesio-distal directions during tooth extraction procedure.

It is to be understood that the term "tooth" as used herein includes, but is not limited to, a healthy tooth, a damaged tooth, a diseased tooth, a fragment of a tooth, such as, a broken root of the tooth.

As used herein, the term "periodontal ligament", commonly abbreviated as PDL, refers to a group of specialized connective tissue fibers that essentially attach cementum of a tooth to the alveolar bone within which it sits. Each ligament has a width of 0.15-0.38 mm. Consisting of mostly Type I and III collagen, the PDL fibers are grouped in bundles and named according to their location, e.g. alveolar crest, horizontal, oblique, periapical, and interradicular fibers.

The periodontal ligament is part of the periodontium which belongs to the tooth attachment system, the supporting structure of a tooth, helping to attach the tooth to surrounding tissues and to allow sensations of touch and pressure. It consists of the cementum, periodontal ligament, alveolar bone, and gingiva. Of these, cementum is the only one that is a part of a tooth. Periodontal ligament connects the alveolar bone to the cementum. Alveolar bone surrounds the roots of teeth to provide support and creates what is commonly called an alveolus, or "socket". Lying over the bone is the gingiva or gum, which is readily visible in the mouth.

Cementum is the tissue covering the dentin of the root of the tooth which is embedded in alveolar bone. Within the root is a root canal, the space occupied by pulp, which extends from the roof of the pulp chamber down into the bottom of each root canal, and opens into the periodontium via the apical foramen. The portion of a tooth which is exposed above the gum is the crown. The enamel covering the crown is highly mineralized whitish substance. Below the enamel is the dentin, which is microscopically porous hard tissue. The pulp chamber located at the center of the tooth houses a pulp which consists primarily of connective tissue, nerve networks and blood vessels.

Any tooth can become damaged or decayed, e.g., due to trauma or due to demineralization of the dental hard tissues by bacterial metabolites (caries). As the decay continues, bacteria often migrate through the porous dentin and infect the pulp. In turn, an immune response to the infection may follow, causing the blood vessels to enlarge and press against the nerves entering the tooth. The result is inflammation of dental pulp (pulpitis).

Another pathologic condition which may affect teeth is periodontal (gum) disease. The primary cause of periodontal disease is the infection caused by a buildup of plaque, an invisible sticky layer of germs that forms naturally on the teeth and gums. Plaque contains bacteria, which produce toxins that irritate the patient's immune system. Impaired host response during chronic infection is the main issue in destruction of periodontal tissues, e.g., due to excessive production of inflammatory mediators, like prostaglandin E2, which induce bone resorption and matrix metalloproteinase (MMP) activation. The activation of MMPs, e.g., MMP-1 and MMP-8, proteolytic enzymes that break the peptide bonds in collagen (collagenases), leads to destruction of periodontal tissues. Eventually, teeth can become loose and may have to be removed.

Various dental procedures for intervening when these or other conditions affecting the oral cavity and its anatomic structures arise are known. These procedures are routinely performed by general dental practitioners, endodontists, prosthodontists, maxillofacial surgeons and peridontists.

The main indication for removal or extraction of the tooth is when the tooth crown is damaged or decayed to an extent that won't allow future reconstruction using any clinically available prosthodontic method. A tooth extraction may also be indicated because of advanced periodontal (gum) disease. Another common reason for removal or extraction of a tooth is when the presence of the tooth is causing crowding, or malocclusion, or preventing another tooth (e.g., a wisdom tooth) from erupting, or in preparation for orthodontic treatment ("braces"). Another condition which dictates tooth extraction is a non-treatable pirapical abscess.

Sometimes, if the crown of the tooth is broken subgingivally, or there are tooth root remnants in the socket, or if the tooth selected for extraction is not fully erupted above the gum, it may be necessary to first remove some of the overlying gum and bone tissue in order to access the tooth for extraction.

In cases wherein the damage to the tooth is irreversible, removal or extraction of the tooth is often indicated. During a simple extraction, a dentist first lifts the tooth with dental elevator and then grasps the tooth with dental forceps, and rocks the tooth back and forth. This rocking motion loosens the tooth from the alveolar bone by breaking the periodontal ligament fibers that hold the tooth anchored to surrounding alveolar bone. The tooth is then pulled from the socket, leaving the tooth socket open.

The methods of replacing teeth include immediate post-extraction dental implant placement. Dental implant is a "root" device, usually made of titanium, used in dentistry to support restorations that resemble a tooth. For immediate implant placement, a-traumatic tooth extraction is critical, to preserve the walls of the extraction socket and improve primary stability of the implant.

As is well known in the field of dentistry the pressure applied by a physician during tooth extraction has a devastating traumatic effect on neighboring tissues such as but not limited to: the soft gum and the alveolar bone underlying the tooth socket. In some cases the pressure applied by a physician during tooth extraction fractures the tooth components such as: crown or roots, increasing tooth extraction difficulty, overall bone loss, and postoperative healing time. The present invention facilitates the process of a-traumatic tooth extraction thereby avoiding or at least reducing the adverse effects of the mechanical extraction procedure.

In one embodiment, the present invention provides a method for extracting a tooth in a subject in need thereof, comprising the steps of a)
applying a composition comprising an effective amount of an agent into the tissue surrounding said tooth, the agent is capable of destroying the periodontal ligament surrounding the tooth; and b) extracting said tooth. In another embodiment, the method of the invention provides numerous advantages, including, but not limited to, minimized trauma to the surrounding tissues selected from gums, bone, and/or blood vessels, minimizing pain associated with tooth extraction and minimizing the duration of the mechanical procedure.

According to some embodiments, the surrounding tissues refers to tissues surrounding the tissue to be extracted, said tissues are selected from gums, bone, and/or blood vessels.

According to specific embodiments the duration of the procedure is reduced in a predictable, reproducible and efficient manner. The decrease in duration of extraction is determined by the amount of enzyme used and the duration of exposure to the enzyme as can be readily determined by the skilled artisan.

According to certain embodiments, the trauma associated with tooth extraction is evident in neighboring tissues such as the gums, the underlying bone plate, blood vessels within the oral cavity or any other tissue in the oral cavity and/or face.

Further advantages of the method of the invention include, avoiding the step of manually severing the gingivodental fibers, including, manually severing the gingivodental fibers with the periosteal elevator, and preventing the formation of broken root tips.

In another embodiment, the method of the invention is beneficial in reducing a risk associated with tooth extraction in a subject in need thereof, by minimizing the need for cutting pieces of the gum and jawbone before extracting a tooth. Furthermore, the method of the invention allows for minimizing the trauma that accompanies a tooth extraction and reducing the dose of anesthetic agent the method of the invention prior to extracting a tooth. Moreover, the method of the invention provides a painless approach or pain reduced platform for extracting a tooth. In fact, the method of the invention requires minimal mechanical pressure (force) for extracting a tooth.

In another embodiment, a risk associated with tooth extraction includes, inter-alia, bleeding, swelling, pain, infection of the extraction site (dry socket), and damage to other teeth or tissue (gum or cheek) in the mouth. A risk associated with tooth extraction may further include, jaw fracture, temporary or permanent injury to the TMJ (jaw-joint), temporary or permanent numbness of the mouth, and life-threatening complications due to the extraction procedure and/or anesthesia. In addition, the risk associated with tooth extraction may be prolonged bleeding, bruising, sinus exposure and oral-antral communication, nerve injury, displacement of a tooth or part of tooth into the maxillary sinus, dry socket (Alveolar osteitis).

It should be noted that the method of the invention is also effective in reducing the psychological effects associated with traumatic surgery. In addition, the method of the invention reduces the systemic side effects, allows treating systemic compromised patients in a private clinic and is suitable for a tooth associated with infections and/or inflammation.

As used herein, the term "extraction", includes, but is not limited to, a simple mechanical extraction performed on a tooth that is visible in the mouth, usually under local anesthetic, and requires only the use of instruments to elevate and/or grasp the visible portion of the tooth, and, an extraction involving surgery, for example, in the case of the removal of a tooth that cannot be easily accessed, either because it is broken under the gum line or because it is not erupted fully.

In another embodiment, extraction, utilizing the methods of the invention, results in expedited healing of the raw open wound overlying the dental socket. In another embodiment, extraction, utilizing the methods of the invention, results in expedited filling of the soft gum tissue. In another embodiment, extraction, utilizing the methods of the invention, results in expedited closure of the socket with bone remodeling.

In another embodiment, the present invention provides a method for placing a dental implant in a subject in need thereof, at a cavity obtained following extracting said tooth. In another embodiment, the method for placing a dental implant in a subject in need thereof comprises the steps of: a) applying a composition comprising an effective amount of an agent to the periodontal ligament surrounding a tooth, the agent is capable of severing the PDL around a tooth, for example, the agent is collagenase; b) extracting said tooth at least 15 minutes after the applying said composition; and c) placing a dental implant at a cavity obtained following extracting said tooth.

The method of the invention for placing a dental implant induces minimal damage to the bone plate of the surrounding alveolar bone and therefore improves the chances of success placement (implantation). Moreover, the method of the invention improves the feasibility of dental implant placement without the need of any supporting bone augmentation surgery.

Without being bound by any mechanism or theory, the present invention is based on the notion that loosening the periodontal ligaments which anchor a tooth to its socket results in an extraction procedure which requires from the dentist performing the tooth extraction procedure, to use reduced force and/or pressure for extraction. The present invention is further based on the notion that loosening the periodontal ligaments which anchor a tooth to its socket results in an extraction procedure characterized by minimal tissue tear in the oral cavity. In addition, loosening the periodontal ligaments (PDLs) which anchor a tooth to its socket results in an extraction procedure characterized by minimal bleeding in the oral cavity and renders redundant rocking a tooth back and forth until the periodontal ligament are broken.

Presumably, loosening of PDLs is achieved by contacting the PDLs with a composition comprising or consisting a collagenase, since collagenase is an enzyme that has the specific ability to digest collagen. Collagenase may be obtained from fermentation by *Clostridium histolyticum*, following purification. Collagenase may be purified by a chromatographic technique. Alternatively, collagenase may be provided as a sterilized lyophilized powder. Optionally, collagenase comprises a minimum assay of 50 ABC units per ml.

According to one embodiment, the agent capable of destroying the periodontal ligament surrounding the tooth is an enzyme. According to another embodiment, said enzyme is capable of cleaving or hydrolyzing collagen peptide bonds. According to yet another embodiment, the enzyme is a proteolytic enzyme. According to yet another embodiment, the enzyme is selected from the group consisting of: dispase, collagenase, proteinase K, hyaluronidase and combinations thereof. Each possibility represents a separate embodiment of the invention.

According to yet another embodiment, the composition further comprises an agent selected from the group consisting of: a pain killer, an anesthetic, an antibiotic, a narcotic, a vitamin, a growth factor and a flavoring agent. Each possibility represents a separate embodiment of the invention.

The composition may further comprise a pharmaceutically acceptable carrier, excipient or diluent.

According to yet another embodiment, the method further comprises applying an effective amount of a deactivation agent into the tissue surrounding said tooth, prior to extracting said tooth and following applying the agent capable of destroying the periodontal ligament surrounding the tooth. According to yet another embodiment, said deactivation agent is a chelating agent.

The term "chelating agent" as used herein, includes, but is not limited to, natural or synthetic agents capable of deactivating metalloenzymes.

According to yet another embodiment, said deactivation agent is ethylenediaminetetraacetic acid (EDTA) or an analogue or derivative thereof. According to yet another embodiment, said deactivation agent is EDTA.

As used herein the term "an analogue or a derivative thereof" includes suitable biologically active variants EDTA. Chemical modification, in the context of the present invention includes modification with a chemical entity, group or moiety. Moreover, each particular compound, such as those described herein, may give rise to an entire family of analogues or derivatives having similar activity and, therefore, usefulness according to the present invention. Likewise, a single compound, such as those described herein, may represent a single family member of a greater class of compounds useful according to the present invention. Accordingly, the present invention fully encompasses not only the compounds described herein, but analogues and derivatives of such compounds, particularly those identifiable by methods commonly known in the art and recognizable to the skilled artisan.

Collagenase may be applied, instilled or injected into the PDL space in a liquid for including a liquid carrier. Following application, the patient's head may be immobilized to avoid substantial movement, for several minutes, e.g., 4 to 120 minutes, in order to minimize expression leakage of the collagenase solution out of the PDL space. Allowing sufficient but not excessive time for action for the collagenase on the PDLs, results in good clinical outcomes.

The collagenase compositions of the invention may be prepared by mixing either a specific number of activity units or specific masses of the preferably purified enzymes. Collagenase is a metalloprotease which requires tightly bound zinc and loosely bound calcium for its activity and is known to digest collagen by hydrolyzing the triple-helical region of collagen under physiological conditions. Collagenase, in some embodiments, consists of two microbial collagenases, referred to as Collagenase AUX I and Collagenase ABC I and Collagenase AUX II and Collagenase ABC II. It is understood that the terms "Collagenase I", "ABC I", "AUX I", "collagenase AUX I", and "collagenase ABC I" mean the same and can be used interchangeably. Similarly, the terms "Collagenase II", "ABC II", "AUX II", "collagenase AUX II", and "collagenase ABC II" refer to the same enzyme and can also be used interchangeably. These collagenases are secreted by bacterial cells. They are isolated and purified from *Clostridium histolyticum* culture supernatant by chromatographic methods. Both collagenases are special proteases and share the same EC number (E.C 3.4.24.3).

Collagenase AUX I has a single polypeptide chain consisting of approximately 1000 amino acids with a molecular weight of 115 kDa. Collagenase AUX II has also a single polypeptide chain consisting of about 1000 amino acids with a molecular weight of 110 kDa. Even though the literature indicates that there are sequence homologies in regions of collagenase AUX I and AUX II, the two polypeptides do not seem to be immunologically cross reactive as indicated by the western blot analysis. The drug substance (collagenase concentrate) has an approximately 1 to 1 mass ratio for collagenase AUX I and AUX II. The collagenase concentrate has an extinction coefficient of 1.528.

Thus, the collagenase composition of the invention may comprise one or more collagenase types, for example, collagenase I, collagenase II, collagenase III or combinations thereof. The collagenase composition may further comprise a broad specificity towards all types of collagenase. The collagenase composition may comprise 1 to 1 mass ratio of collagenase I to collagenase II, 1.5-10 to 1 mass ratio of collagenase I to collagenase II, 1 to 1.5-10 mass ratio of collagenase I to collagenase II, 1 to 2 ratio of collagenase I and collagenase II, among other options. In some embodiments, combining several collagenase types improves the synergistic activity provided by the different collagenases resulting in superior therapeutic benefit.

In another embodiment, a collagenase of the invention is a combination of collagenase I and collagenase II having synergistic activity toward collagen. In another embodiment, collagenase activity is measured by the enzyme's ability to hydrolyze either synthetic peptide or collagen substrate. Those skilled in the art will recognize that enzyme assays other than those disclosed herein may also be used to define and prepare functionally equivalent enzyme compositions.

In another embodiment, pharmaceutical formulations comprise a therapeutically effective amount of a collagenase composition of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, perfuming agents, preservatives and antioxidants can also be present in the composition, according to the judgment of the formulator.

The pharmaceutical composition of the invention may be administered topically, subcutaneously, intraligamentally, intragingivally, or via an implanted reservoir. The composition may be injected or applied by direct instillation into the PDL space. The term "local administration" and "topical administration" as used herein are interchangeable and may include any of the aforementioned direct applications.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic pharmaceutically acceptable diluent or solvent. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In another embodiment, collagenase is applied in a liquid carrier or a gel carrier that is pharmaceutically acceptable, including inertness towards the collagenase. In another embodiment, the liquid carrier is a buffer. In another embodiment, the liquid carrier is an isotonic solution. In another embodiment, the liquid carrier is saline. In another embodiment, the liquid carrier is an aqueous NaCl/CaCl$_2$ buffer. In another embodiment, the liquid carrier is a dextran solution. In another embodiment, collagenase is applied in a heptastich solution.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. The sterile solutions may also be lyophilized for later use.

Dosage forms for administration of collagenase of this invention include gels, solutions, or sprays. Collagenase may be admixed under sterile conditions with a pharmaceutically acceptable carrier and any needed preservatives or buffers as may be required. Gels, in some embodiments, contain, in addition to collagenase of this invention, excipients such as animal and vegetable fats, oils, waxes, paraffin, starch, tragacanth, cellulose derivatives, polyethylene glycols, silicones, bentonites, silicic acid, talc and zinc oxide, or mixtures thereof. Sprays, in some embodiments, in addition to the compounds of this invention, include excipients such as lactose, talc, silicic acid, aluminum hydroxide, calcium silicates and polyamide powder, or mixtures of these substances. Sprays, in some embodiments, additionally contain customary propellants such as but not limited to chlorofluorohydrocarbons.

In another embodiment, collagenase of the invention is a lyophilized injectable composition formulated with lactose. In one embodiment, each milligram of injectable collagenase is formulated with 1-4 mg of lactose. In another embodiment, each milligram of injection collagenase has approximately 1000-3000 SRC units and 10000-51000 units measured with a potency assay using a synthetic substrate, pzGPGGPA.

In another embodiment, the collagenase composition of the invention is a lyophilized injectable composition formulated with Sucrose, Tris at a pH level of about 6.0-8.0.

In another embodiment, the collagenase composition of the invention is administered by intraligamental injection. In another embodiment, the collagenase composition of the invention is administered by computer-controlled injection delivery system into the PDL space. In another embodiment, the collagenase composition is soaked onto a subgingival cord and thereby administered to the PDL space.

In another embodiment, the collagenase composition of the invention further includes an antibiotic, an anti-inflammatory agent, an anti-septic agent, an anesthetic agent or any combination thereof.

In another embodiment, the term "therapeutically effective amount" and "effective amount" of a compound of the invention as used herein are interchangeable and refer to an amount of the compound which confers loosening of PDLs anchoring in a given tooth. Typically, different amounts and/or concentrations of the composition of the invention are applied to different teeth (i.e. molars versus incisors). Therefore, a therapeutic effect is achieved with different amounts and/or concentrations depending on the particular tooth to be extracted, and also depending on the age (child, adult, etc.) and the dental condition as assessed by one of skill in the art.

It will be understood, however, that the total dosage of the compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts. In another embodiment, the amount and concentration of collagenase are effective in loosening the PDLs. In another embodiment, the term "loosening" as used herein includes softening, relaxing, or rupturing. In another embodiment, the method of the invention reduces the tension exerted by the PDLs that have been holding the tooth and the gums in close-fitting.

In some embodiments, the effective amount and concentration of collagenase is at least 1,000 ABC units per ml of carrier, at least 2,000 ABC units per ml of carrier, at least 3,000 ABC units per ml of carrier, within the range of 2,000 to about 8,000 ABC units per ml of carrier, within the range of about 3,000 to about 25,000 ABC units per ml of carrier. In general, the lower the amount of collagenase, the greater should be the concentration. Thus, if in a particular situation it is desired to use 2,000 ABC units, a concentration of 8,000 to 20,000 units/ml would be desirable.

In another embodiment, the total volume of the composition applied/injected does not exceed about 1 ml. In another embodiment, the total volume of the composition applied/injected does not exceed about 0.8 ml. In another embodiment, the total volume of the composition applied/injected does not exceed about 0.5 ml. In another embodiment, the total volume of the composition applied/injected does not exceed about 0.4 ml. In another embodiment, the total volume of the composition applied/injected does not exceed about 0.1 ml. In another embodiment, the total volume of the composition applied/injected does not exceed about 0.05 ml. In another embodiment, the total volume of the composition applied/injected does not exceed about 0.01 ml. In another embodiment, the total volume of the composition applied/injected does not exceed about 0.005 ml. In another embodiment, the total volume of the composition applied/injected does not exceed about 0.001 ml. In another embodiment, the total volume of the composition applied/injected does not exceed about 0.0005 ml.

In another embodiment, the total dosage of the collagenase composition per PDL space of a tooth is applied, (for example, by injection), in a plurality of locations and portions, in at least two locations and portions, in at least three locations and portions or in at least four locations and portions. In yet another embodiment, the total dosage of the collagenase composition per PDL space of a tooth is applied at different loci around the tooth destined to extraction. In another embodiment, at least 8 portions or loci are subject to application, e.g. by injection.

In another embodiment, the different loci around the tooth destined to extraction are in close proximity to each other (less than 2 mm apart from one another). In another embodiment, the composition is applied by injection, where the needle of the injection syringe is not be inserted at an acute angle a to the PDL space, but is rather inserted at right angle, in order to assure good distribution of the collagenase within a small volume of the PDL space.

In another embodiment, a subject in need thereof is a human subject. In another embodiment, a subject is a pet, a mammal or a farm animal.

In another embodiment, a subject in need thereof is a subject in need of a tooth extraction. In another embodiment, a subject in need thereof is a subject having at least one tooth that is severely damaged by caries. In another embodiment, a subject in need thereof is a subject afflicted with a periodontal disease. In another embodiment, a subject in need thereof is a subject having at least one tooth with peri-apical infection that can neither be preserved endodontically nor by surgery and have caused an extensive inflammation (e.g. of the maxillary sinus or the soft tissue) or a cyst. In another embodiment, a subject in need thereof is a subject having at least one tooth damaged by trauma (multiple fractures, longitudinal fracture, and extensive bony defect in the periodontal region). In another embodiment, a subject in need thereof is a subject afflicted with crowding or impeded eruption (milk teeth and permanent teeth should be extracted for orthodontic reasons). In another embodiment, a subject in need thereof is treated by a prosthodontic treatment in order to maintain normal occlusion (elongated or heavily tilted teeth, particularly with previous contacts).

In another embodiment, a subject in need thereof is a subject afflicted with cancer, during tumor surgery, and at least one tooth is located within the area of the tumor. In another embodiment, a subject in need thereof is a subject undergoing focal restoration (in cases of neuralgia, extraction is often performed without clinical and radiological findings). In another embodiment, a subject in need thereof is a subject afflicted with trigeminal neuralgia (prosopalgia). In another embodiment, a subject in need thereof is a subject afflicted with focal infection (the physician will decide according to the underlying disease). In another embodiment, a subject in need thereof is a subject afflicted with endocarditis. In another embodiment, a subject in need thereof is a subject afflicted with acute rheumatic fever. In another embodiment, a subject in need thereof is a subject afflicted with acute glomerulonephritis.

In another embodiment, a subject in need thereof is a subject suffering from acute tooth pain. In another embodiment, a subject in need thereof is a subject suffering from initial and severe inflammatory complications of general disease(s). In another embodiment, a subject in need thereof is a subject suffering from an acute infection (abscess). In another embodiment, a subject in need thereof is a subject in of wisdom teeth extraction. In another embodiment, a subject in need thereof is a subject in of wisdom teeth extraction before completion of orthodontic therapy.

In another embodiment, a subject in need thereof is a subject afflicted with a bleeding disorder. In another embodiment, a subject in need thereof is a subject afflicted with diabetes. In another embodiment, a subject in need thereof is a subject afflicted with a heart disease. In another embodiment, a subject in need thereof is a subject afflicted with a disease affecting the immune system.

According to one embodiment, the present invention provides a kit for extracting a tooth, the kit comprises a first container comprising a composition comprising an effective amount of an agent capable of destroying the periodontal ligament surrounding the tooth into the tissue surrounding said tooth. According to yet another embodiment, the kit further comprises an additional composition comprising an agent, selected from the group consisting of: a pain killer, an anesthetic, an antibiotic, a narcotic, a vitamin, a growth factor, a flavoring agent and combination thereof. According to yet another embodiment, the kit further comprises a composition comprising an effective amount of a deactivation agent. According to yet another embodiment, the kit further comprises dental means for extracting said tooth. According to yet another embodiment, the kit further comprising instructions manual, listing the use of each component of the kit and the sequence of use. According to yet another embodiment, the instruction manual describes the use of the kit according to the method of the invention.

According to yet another embodiment, the instruction manual describes the use of the kit according to the method of the invention, as follows: (a) apply the composition comprising an effective amount of the agent capable of destroying the periodontal ligament surrounding the tooth into the tissue surrounding the tooth to be extracted, and, optionally, prior to applying, mix said composition with said additional composition comprising an agent, selected from the group consisting of: a pain killer, an anesthetic, an antibiotic, a narcotic, a vitamin, a growth factor, a flavoring agent and combination thereof; (b) optionally, allow a delay of 15 minutes to 3 hours after (a) and prior to extracting said tooth; (c) optionally, or alternatively, apply the composition of deactivation agent into the tissue surrounding said tooth, prior to extracting said tooth; and (d) extract said tooth.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1

Defragmentation of Gingival Tissue In Vitro by Collagenase

A. Dimension Measurement Using a Millimetric Grid

Gingival tissue was chosen for the purpose of In vitro experiments, as it can be easily obtained at various sizes and has many common characteristics with PDL, where PDL is too thin and delicate for this kind of experiments.

A band of gingival tissue, $20 \times 3 \times 0.3$ mm$^3$, was obtained from the diastema region of pig mandible within a few minutes following sacrifice. The band was sliced into four equal specimens about $5 \times 3 \times 0.3$ mm$^3$ each (FIG. 1 and FIG. 2A).

Two specimens were conditioned in 0.5 ml of phosphate-buffered saline (PBS) containing 5450 units/ml collagenase CLPSA solution (Worthington Biochemical Corporation, NJ, USA; FIGS. 2D and 2E) and two specimens were conditioned in 0.5 ml PBS (FIGS. 2B and 2C) and served as control. All four specimens were incubated in 37° C. water bath under gentle agitation for different time intervals.

The extent of tissue degradation was determined by measuring the overall volume of each specimen, by placing the specimen over a millimetric grid, after 3 hours or after 24 hours of incubation with PBS or with collagenase.

The results indicate that the volume of specimen incubated with collagenase decreased by more than 60%, to $5 \times 3 \times 0.1$ mm$^3$, after 3 hours of incubation (FIG. 2D), while the slice was defragmented to immeasurable specimens after 24 hours of incubation with collagenase (FIG. 2E). The volume of the control specimen did not change after 3 hours or 24 hours incubation with PBS (FIGS. 2B and 2C, respectively) relative to the original specimen (FIG. 2A).

B. Histophathological Examination of Collagen Degeneration

Collagen degeneration can be observed using hematoxylin and eosin (H&E) staining but it is better visualized under polarized light on Picrosirius Red (PSR). To this end, punch biopsies from the hard palate containing oral masticatory mucosa were obtained. A volume of 50 μl containing 2,500, 5,000, 7,500 or 10,000 units/ml of collagenase CLPSA solution (Worthington Biochemical Corporation, NJ, USA) was injected right below the ridge of the palatal rugae in the center of the tissue, as shown in FIG. 3A.

Figure 3B:
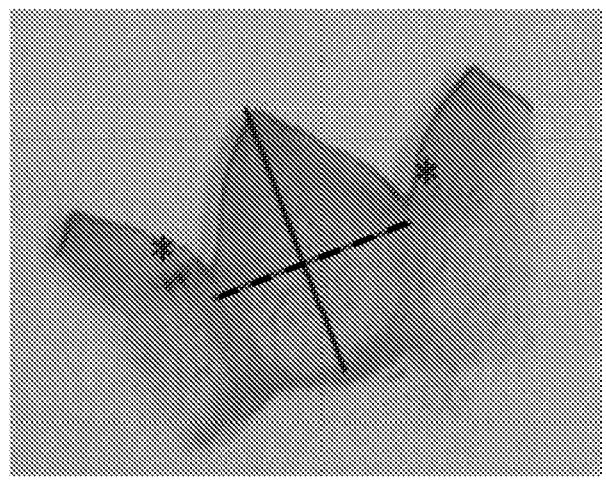

In order to mark the area of injection, Indian ink was injected, prior to fixation, parallel to the loci of collagen/PBS/ink injection, on both sides of the punch, as shown in FIG. 3B by asterisks on both sides of a broken horizontal white line. For assessing areas of collagen degeneration, each slice was marked by a horizontal line (FIG. 3B—broken while line; Table 1—Ridge horizontal) which is parallel to the ridge line and with a vertical line (FIG. 3B—black line; Table 1—Ridge vertical) crossing the horizontal line and which is perpendicular to the ridge line.

Figure 4A:
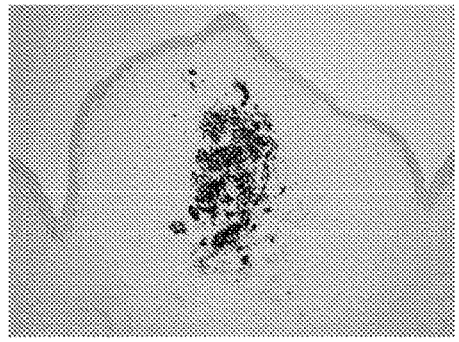
FIGS. 4A-4F represent fixed H&E stained tissue specimen following injection of ink (FIG. 4A) as viewed under light microscope and Picrosirius red stained tissue specimens following injection of PBS (FIG. 4B) or different concentrations of collagenase (FIGS. 4C-4F) as viewed under on a microscope under polarized light.
Figure 4B:
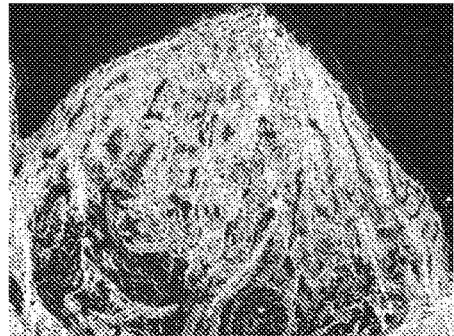
Figure 4C:
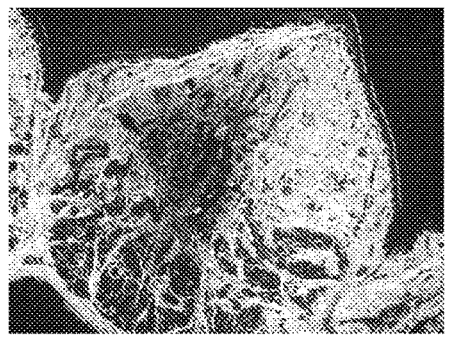
Figure 4D:
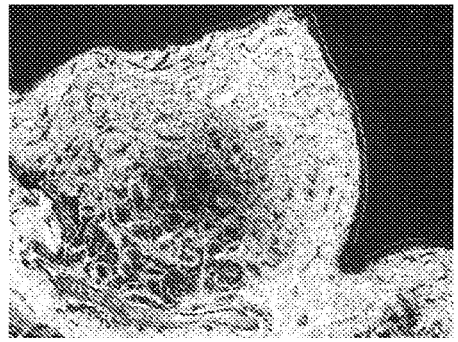

Control groups consisted of non-treated (non-injected) samples and specimens that were injected with PBS (FIGS. 4A and 4B). These groups were incubated under conditions similar to the conditions of the treatment groups. Punch tissue specimen were incubated in PBS for 0, 2, 5, 12 and 24 hours at 37° C. prior to fixation by formalin.

After fixation, tissues were trimmed, embedded in paraffin and sectioned longitudinally at the level of the injection site (marked by the ink), then stained with Hematoxylin & Eosin, Masson's trichrome (MT) and Picrosirius Red (PSR) and transferred to histopathological examination. The size (in mm) of each slice before and after treatment was assessed along the vertical line (Table 1—Ridge vertical) and along the horizontal line (Table 1—Ridge horizontal). Representative specimen are shown in FIG. 4 as follows: (A) Sample #56—control injected solely with ink, Hematoxylin & Eosin stain; (B) Sample #31—control injected with PBS, Picrosirius Red (PSR) stain, viewed under polarized light; (C) Sample #33—injected with collagenase 2,500 unit/ml Picrosirius Red (PSR) stain, viewed under polarized light; (D) Sample #35—injected with collagenase 5,000 unit/ml Picrosirius Red (PSR) stain, viewed under polarized light; (E) Sample #37—injected with collagenase 7,500 unit/ml Picrosirius Red (PSR) stain, viewed under polarized light; and (F) Sample #39—injected with collagenase 10,000 unit/ml Picrosirius Red (PSR) stain, viewed under polarized light.

Tissue structure after 2 and 5 hours following treatment is summarized in Tables 1 and 2, respectively.

Figure 4E:
Figure 4F:
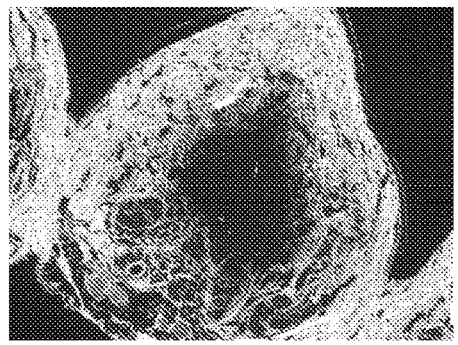

Pathological examination revealed major collagenolysis, in a dose dependent manner, of all treated specimens compared to control groups. As shown in FIG. 4 and further described in Tables 1 and 2, the areas of gingival tissue degeneration were presented by pale staining and thinner collagen bundles, pale staining of adipose tissue cell membrane and hypereosinophillia and granularity of the wall of small arteries. The largest area of degeneration was observed in a sample treated with 7,500 unit/ml of collagen (FIG. 4E). The control samples (FIGS. 4A and 4B, respectively) were within normal ranges.

TABLE 1

| | Tissue structure 2 hours post injection with ink. PBS or collagenase (Coll.) | | | | | |
|---|---|---|---|---|---|---|
| Sample No. | Injection (units/ml) | Ridge vertical (mm) | Ridge horizontal (mm) | Collagen degeneration, vertical (mm) | Collagen degeneration horizontal (mm) | Comments |
| 1 | None | 7.0 | 5.5 | 0 | 0 | Normal ranges, no evidence of collagenolysis, tissue is homogenous on PSR |
| 2 | PBS | 5.4 | 6.1 | 0 | 0 | Normal ranges, no evidence of collagenolysis, tissue is homogenous on PSR |
| 3 | Coll. 2,500 | 6.25 | 5.0 | 2.5 | 2.75 | Pale staining of collagen bundles in the submucosa, with hypereosinophillia and coarse appearance of collagen of the small arterial walls |
| 4 | Coll. 5,000 | 5.35 | 5.5 | 1.0 | 1.5 | Pale staining of collagen bundles in the submucosa. The area involves collagen in the submucosa and submucosal fat. There is hypereosinophillia of rare small arterial walls. |
| 5 | Coll. 7,500 | 6.5 | 5.15 | 3.0 | 4.0 | Extensive pale staining of submucosa collagen and adipocyte cell membrane. Rupture of fat cells. |

TABLE 1-continued

Tissue structure 2 hours post injection with ink. PBS or collagenase (Coll.)

| Sample No. | Injection (units/ml) | Ridge vertical (mm) | Ridge horizontal (mm) | Collagen degeneration, vertical (mm) | Collagen degeneration horizontal (mm) | Comments |
|---|---|---|---|---|---|---|
| 6 | Coll. 10,000 | 7.5 | 5.75 | 2.0 | 2.37 | Hypereosinophillia and coarse appearance of collagen of the small arterial walls. Pale staining of collagen bundles and adipocyte cell membrane in the submucosa. Coarse and hypereosinophillic staining of rare arterioles. |

TABLE 2

Tissue structure 5 hours post injection with ink. PBS or collagenase (Coll.)

| Species No. | Description | Histological findings |
|---|---|---|
| 56 | Control (ink) | A single localized focus of black staining within the submucosa in the exact center of the tissue section. The sample was used as an internal control for confirmation of adequate section site (see, FIG. 4A) |
| 29 | Control | Tissue within normal ranges, no evidence of collagenolysis. On MT and PSR under polarization the tissue is homogenous |
| 31 | Control, PBS) | Tissue is within normal ranges, no evidence of collagenolysis. On MT and PSR under polarization the tissue is homogenous, (see, FIG. 4B) |
| 33 | Coll. 2,500 | On H&E stains, there is a single localized focus of paler staining within the submucosa in the center of the tissue section. On PSR stain under polarized light, the described pale focus is not birefringent, leaving a dark space in the section (see, FIG. 4C) |
| 35 | Coll. 5,000 | On H&E and MT stains, there is a single localized area of paler staining within the submucosa in the center of the tissue section. On PSR stain under polarized light, the described pale focus in not birefringent, leaving a dark space in the section (see, FIG. 4D). This area is ca. 1.5 × 1.0 mm in size |
| 37 | Coll. 7,500 | On H&E and MT stains, there is a single localized area of paler staining within the submucosa in the center of the tissue section. On PSR stain under polarized light, the described pale focus in not birefringent, leaving a dark space in the section (see, FIG. 4E). This area is ca. 2.0 × 2.0 mm in size |
| 39 | Coll. 10,000 | On H&E and MT stains, there is a single localized area of paler staining within the submucosa in the center of the tissue section. On PSR stain under polarized light, the described pale focus in not birefringent, leaving a dark space in the section (see, FIG. 4F). This area is ca. 2.2 × 2.0 mm in size |

Example 2

Assessment of the Intraligamental Injection Volume Ex-Vivo

Assessment was based on empirical findings regarding the length of the teeth to be treated and the width of the periodontal ligament at specific sections. This data was used to calculate the estimated PDL volume. This estimation was then reevaluated clinically.

Indian ink was injected into the PDL of mandibular 3rd incisor and 1st premolar, at 6 points. The end point was determined by the injection volume causing dye leakage. The optimal volume was determined as 20 μl at each of the 6 points of injection.

Example 3

PDL Defragmentation Following Collagenase Injection

Figure 5:
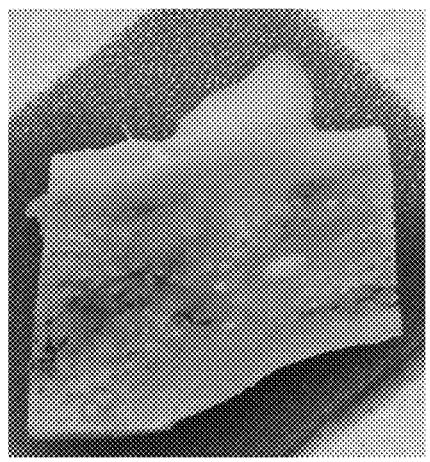
FIG. 5 shows a fixed, decalcified slice of a mandible specimen, containing a tooth embedded in the bone socket, post injection.

In order to evaluate PDL structure rather than gingival structure, mandibular 3rd incisor and 1st premolar bilaterally and the tissue surrounding same, were subjected to enzyme injection (20 μl at 6 points) at different concentrations (2,500; 5,000; 7,500 or 10,000 units/ml). Two hours post injection the mandibles were cut and trimmed around the relevant tooth, leaving a tooth embedded in the bone socket, and fixed in formalin. Specimens were decalcified for 5-6 days, then trimmed (FIG. 5), embedded in paraffin and sectioned along the tooth's long axis.

The sections were stained with Hematoxylin & Eosin and Picrosirius Red and transferred to histopathological examination in order to test PDL collagen fibers breakdown at different sections of the root and integrity of surrounding tissues structures (alveolar bone proper). Specimen that were injected with PBS or not injected served as control.

PDL Defragmentation was Observed Following Collagenase Treatment.

Example 4

Tooth Extraction Ex Vivo

Figure 6:
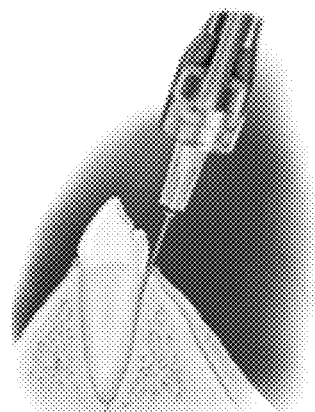
FIG. 6 is a schematic presentation of intraligamental injection.

Mandibular 3rd incisor and 1st premolar bilaterally, obtained 4 hours after animal was sacrificed, were subjected to intraligamental enzyme injection (20 μl at 6 points) at different concentrations (2,500; 5,000; 7,500 or 10,000 units/ml), as shown for example in FIG. 6. Two hours post injection the teeth were extracted using standard dental forceps, along the long axis of the tooth, without applying rotational forces. Ease of extraction was determined relative to control (non-injected and PBS injected) teeth.

Figure 7A:
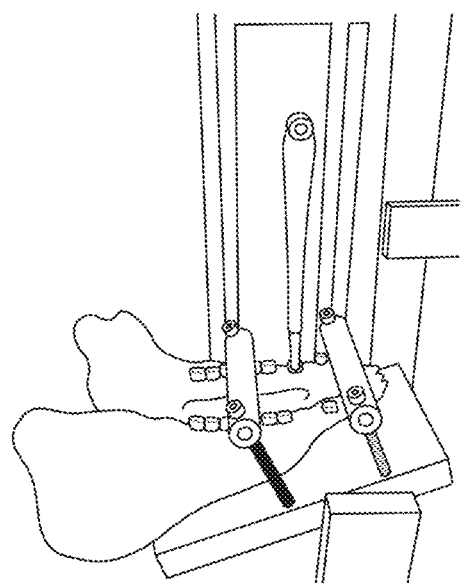
FIGS. 7A-7B exhibit an electronic device for measuring the amount of force required for tooth extraction (FIG. 7A). A close up view of the device (FIG. 7B) presents, the dental that grasps the crown of the tooth (arrow). Also shown are two axis mobile means that holds the mandible, having four adjustable screws.
Figure 7B:
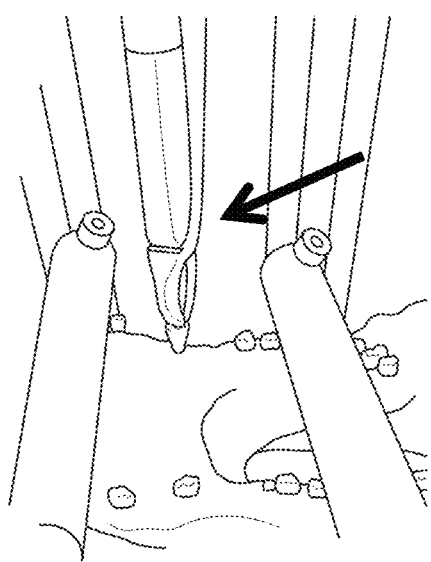

The amount of force required for extraction was measured using an electronic device for tooth extraction, measuring the force applied in kgf units (FIGS. 7A-7B). Using the device, the crown of the tooth was firmly held by the dental forceps tightened with a screw. The jaw bone was held separately by two axis means capable of holding the mandible by four adjustable screws. The mandible was positioned in a manner enabling extraction by applying the force along the long axis of the root, namely, pulling out the tooth from the bone/tooth socket in an upwards direction.

Manual extraction of teeth that were injected with collagenase solution (10,000 units/ml) was significantly easier, namely, required investing significantly less force, than the force required for extracting non treated teeth. Moreover, while the treated teeth were extracted in one piece, several crowns broke during extraction of the non-treated teeth.

Example 5

Tooth Extraction In Vivo

Six-month old domestic pig is anesthetized. A series of intraligamental injections of a composition comprising an effective amount of collagenase is administered at 6 locations around the tooth. About 30 minutes after collagenase intraligamental injections, the site is washed with EDTA.

The tooth is extracted by pulling the tooth from the bone socket in an upwards direction, using force along the long axis of the tooth and without using rotational forces. Extraction is carried out using dental forceps or an elevator. The elevator is inserted into the mesial or distal PDL space (no need for firm apical pressure), with the concave side toward the tooth to be extracted. The elevator is rotated in such a way as to move the tooth toward the facial.

After the tooth is properly elevated, it is luxated and extracted.

The amount of force required for extraction is evaluated using the extraction device. The results are compared with the force required for extraction of a non-treated tooth.

Example 6

Socket Preservation

Bone and associated soft tissue are important considerations when replacing teeth. If an implant is to be placed, there must be adequate bone for the fixture, and correct manipulation of gingival tissue is essential for an esthetically pleasing outcome. If bone loss is severe, a removable dental prosthesis (RDP) should be considered.

Applying the a-traumatic extraction method of the invention reduces the duration of healing of the incisor extraction site by at least 50%. Moreover, there is no apparent decrease in alveolar ridge height and width within the first 6 months following tooth extraction. The bone associated with the adjacent mesial and distal dental surfaces is at its original vertical dimension. Thus socket preservation is obtained. Hence, treating the PDL space with collagenase enhances socket preservation and thereby increases the chances of successfully implanting a dental implant.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

What is claimed is:

1. A method for extracting a tooth in a subject in need thereof, the method comprising:
   injecting into the tissue surrounding said tooth a composition comprising collagenase;
   applying, after 0.25 to 3 hours, an extraction force parallel to the long axis of said tooth; and
   extracting said tooth.

2. The method of claim 1, wherein the composition is contacted with at least one locus at the periodontal ligament space surrounding the tooth.

3. The method of claim 1, wherein said collagenase is selected from the group consisting of collagenase I, collagenase II, collagenase III and a combination thereof.

4. The method of claim 3, wherein said composition comprises 1 to 1 mass ratio of collagenase I to collagenase II.

5. The method of claim 1, wherein said composition has an effective volume of 0.01 to 3 ml.

6. The method of claim 1, wherein said composition further comprises an agent, selected from the group consisting of: a painkiller, an anesthetic, an antibiotic, a vitamin, a growth factor, a flavoring agent and combination thereof.

7. A method for extracting a tooth in a subject in need thereof, the method comprising:
   injecting into the tissue surrounding said tooth a composition comprising synthetic collagenase;
   applying, after 0.25 to 3 hours, an extraction force parallel to the long axis of said tooth;
   extracting said tooth; and
   placing a dental implant at a cavity obtained following the step of extracting said tooth.

8. The method of claim 7, wherein the composition is contacted with at least one locus at the periodontal ligament space surrounding the tooth.

9. The method of claim 7, wherein said synthetic collagenase is selected from the group consisting of synthetic collagenase I, synthetic collagenase II, synthetic collagenase III and a combination thereof.

10. The method of claim 9, wherein said composition comprises 1 to 1 mass ratio of synthetic collagenase I to synthetic collagenase II.

11. The method of claim 7, wherein said composition has an effective volume of 0.01 to 3 ml.

12. The method of claim 7, wherein said composition further comprises an agent, selected from the group consisting of: a painkiller, an anesthetic, an antibiotic, a vitamin, a growth factor, a flavoring agent and combination thereof.

13. A method for extracting a tooth in a subject in need thereof, the method comprising:
   injecting into the tissue surrounding said tooth a composition consisting of collagenase;
   applying, after 0.25 to 3 hours, an extraction force parallel to the long axis of said tooth; and
   extracting said tooth.

14. The method of claim 13, wherein the composition is contacted with at least one locus at the periodontal ligament space surrounding the tooth.

15. The method of claim 13, wherein said collagenase is selected from the group consisting of collagenase I, collagenase II, collagenase III and a combination thereof.

16. The method of claim 15, wherein said composition comprises 1 to 1 mass ratio of collagenase I to collagenase II.

17. The method of claim 13, wherein said composition has an effective volume of 0.01 to 3 ml.

\* \* \* \* \*